United States Patent [19]

Ebel et al.

[11] Patent Number: 4,670,558
[45] Date of Patent: Jun. 2, 1987

[54] AMINOALKYLMELAMINES

[75] Inventors: Klaus Ebel, Ludwigshafen; Wolfgang Reuther, Heidelberg, both of Fed. Rep. of Germany

[73] Assignee: BASF Aktiengesellschaft, Ludwigshafen, Fed. Rep. of Germany

[21] Appl. No.: 788,466

[22] Filed: Oct. 17, 1985

[30] Foreign Application Priority Data

Oct. 23, 1984 [DE] Fed. Rep. of Germany ....... 3438694

[51] Int. Cl.$^4$ .............................................. C07D 251/70
[52] U.S. Cl. .................................... 544/196; 544/197
[58] Field of Search ................................ 544/196, 197

[56] References Cited

U.S. PATENT DOCUMENTS

| 2,545,049 | 3/1951 | Schaefer et al. | 260/249.6 |
| 3,700,671 | 10/1972 | D'Alelio | 544/196 |
| 3,755,322 | 8/1973 | Winter et al. | 544/196 |
| 3,879,389 | 4/1975 | Kan et al. | 260/249.6 |
| 4,514,399 | 4/1985 | Regnier et al. | 544/196 |

FOREIGN PATENT DOCUMENTS

| 49-39272 | 10/1974 | Japan | 544/196 |
| 867279 | 3/1961 | United Kingdom . | |

OTHER PUBLICATIONS

Kirk-Othmer, "Encyclopedia of Chemical Technology", 2nd Edition, vol. 21, pp. 77–80, 94 and 95 (1970).
Houben-Weyl, "Methoden der Organischen Chemie", vol. 14, part 2, pp. 80–83, 169 and 170 (1963).
Kirk-Othmer, "Encyclopedia of Chemical Technology", 3rd Edition, vol. 7, pp. 591–596 (1979).
Kaiser et al., J. Am. Chem. Soc. 73 (1951), pp. 2984–2986.
Borkovec et al., J. Med. Chem. 10 (1967), pp. 457–461.
Mosher, J. Am. Chem. Soc. 67 (1945), pp. 662–664.

*Primary Examiner*—John M. Ford
*Attorney, Agent, or Firm*—John H. Shurtleff

[57] ABSTRACT

Preparation of amidoalkylmelamines and aminoalkylmelamines of the formula I

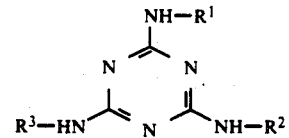

where $R^1$ is an amidoalkyl group —$(CH_2)_n$—NHZ or an aminoalkyl group —$(CH_2)_n$—$NH_2$, n is from 2 to 10, preferably from 2 to 6, Z is an amino protective group and $R^2$ and $R^3$ independently of one another are each hydrogen or have the same meanings as $R^1$, are prepared by a process in which a chlorotriazine is reacted with a diamine of the formula $H_2N$—$(CH_2)_n$—NHZ, where n and Z have the above meanings, to give an amidoalkylmelamine, and, if required, the group Z is eliminated.

4 Claims, No Drawings

AMINOALKYLMELAMINES

The present invention relates to a process for the preparation of amidoalkylmelamines and aminoalkylmelamines of the general formula I

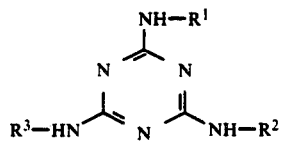

where $R^1$ is an amidoalkyl group —$(CH_2)_n$—NHZ or an aminoalkyl group —$(CH_2)_n$—$NH_2$, n is from 2 to 10, preferably from 2 to 6, Z is an amino protective group, and $R^2$ and $R^3$ independently of one another are each hydrogen or have the meanings stated for $R^1$, and the novel amido- and aminoalkylmelamines obtained in this manner.

N-Alkyl-substituted and N-aryl-substituted melamines can be prepared as described by Kaiser et al., J. Am. Chem. Soc. 73 (1951), 2984-2986, by converting cyanuric chloride, dichloroaminotriazine or diaminochlorotriazine. 2,4,6-Tris-(alkanolamino)-triazines have been prepared in a similar manner (U.S. Pat. No. 3,879,389).

Of the aminoalkylmelamines obtainable according to the invention, only N-mono-(2-aminoethyl)-melamine and N-mono-(6-aminohexyl)-melamine have been described to date. They are prepared by reacting diaminochlorotriazine with the corresponding alkylenediamines.

N-Mono-(2-aminoethyl)-melamine, in the form of the hydrated hydrochloride, is characterized in J. Med. Chem. 10 (1967), 457–461 by means of an elemental analysis, but no method of preparation is stated. It is therefore assumed that the product obtained was not N-mono-(2-aminoethyl)-melamine or in any case not pure N-mono-(2-aminoethyl)-melamine.

N-Mono-(6-aminohexyl)-melamine has been characterized by a melting point of 154° C. in J. Am. Chem. Soc. 67 (1945), 662–664, but no method of preparation is given, this being described in British Pat. No. 867,279. The melting point stated there is 175°–177° C.

In contrast, N,N'-bis- and N,N',N''-trisaminoalkylmelamines were unknown to date. This is obviously due to the fact that the reaction of chlorotriazines or aryloxytriazines with alkylenediamines leads preferentially to polymeric products (U.S. Pat. No. 2,545,049).

It is an object of the present invention to provide a novel route which permits the synthesis of aminoalkylmelamines and makes it possible to prepare not only the N-mono-(aminoalkyl)-melamines but also the N,N'-bis- and N,N',N''-tris-(aminoalkyl)-melamines.

We have found that this object is achieved by a process for the preparation of amidoalkylmelamines and aminoalkylmelamines of the general formula I

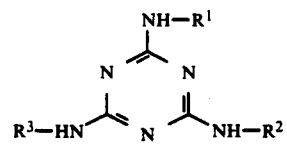

where $R^1$ is an amidoalkyl group —$(CH_2)_n$—NHZ or an aminoalkyl group —$(CH_2)_n$—$NH_2$, n is from 2 to 10, preferably from 2 to 6, Z is an amino protective group, and $R^2$ and $R^3$ independently of one another are each hydrogen or have the meanings stated for $R^1$, wherein the chlorotriazine is reacted with a diamine of the general formula $H_2N$—$(CH_2)_n$—NHZ, where n and Z have the above meanins, to give an amidoalkylmelamine, and, if required, the latter is converted to an aminoalkylmelamine by eliminating the group Z.

The principle of the synthesis is represented by the following equations:

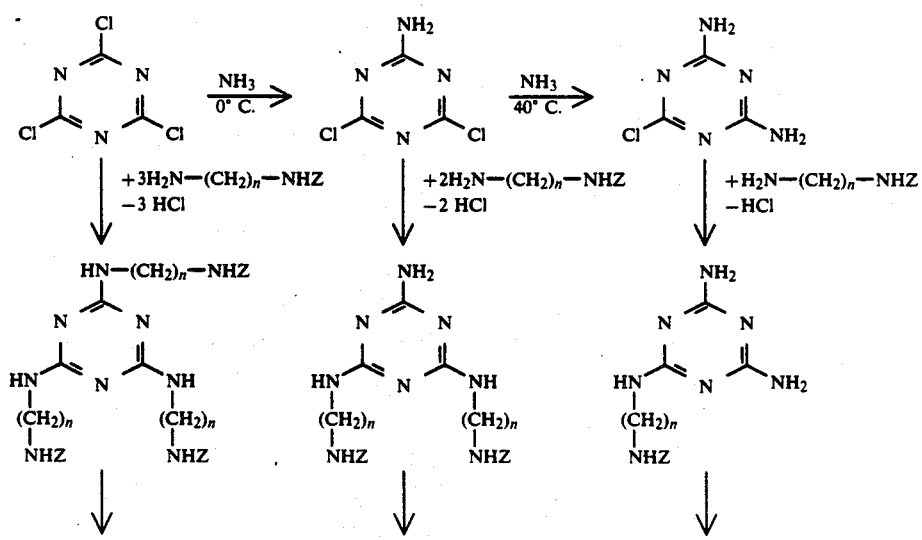

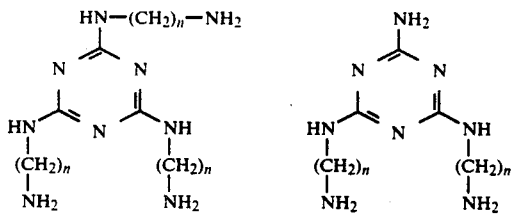 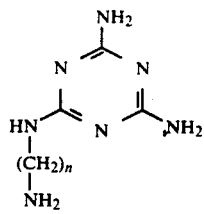

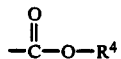

The amidoalkylmelamines are prepared starting from cyanuric chloride or from the diaminochlorotriazine or dichloroaminotriazine obtainable from cyanuric chloride by reaction with ammonia. All three educts are disclosed in J. Am. Chem. Soc. 73 (1951), 2984, and are reacted with alkylenediamines, blocked at one end with a protective group Z, to give amidoalkylmelamines by a method similar to that described there for alkylamines.

Suitable groups for protecting the amino group are the formyl or tosyl radical and, in particular, the acetyl group, which may be unsubstituted or substituted by halogen, eg. fluorine or chlorine, and groups of the formula $$-\overset{\overset{O}{\|}}{C}-O-R^4$$

where $R^4$ is straight-chain or branched alkyl of 1 to 15, in particular 1 to 6, carbon atoms, cycloalkyl of 5 to 8 carbon atoms, aryl which is unsubstituted or substituted by alkyl of 1 to 8, in particular 1 to 4 carbon atoms, or aralkyl of 7 to 12 carbon atoms. The radicals stated for $R^4$ may be further substituted by groups which are inert under the reaction conditions, eg. nitro, halogen or alkoxy.

Particular examples of amino protective groups are acetyl, trifluoroacetyl, methoxy, ethoxy, tert.-butoxy, cyclopentyloxy and phenoxycarbonyl, as well as carbobenzyloxy and para-nitrobenzyloxy.

The reaction of the chlorotriazines with the alkylenediamines —$H_2N$—$(CH_2)_n$—NHZ which are protected at one end and in which n is from 2 to 10, in particular from 2 to 6, can be carried out in an organic solvent, eg. dioxane, but is preferably effected in aqueous solution.

The alkylenediamines protected at one end are added, as a rule, in an excess amount with respect to the corresponding chlorotriazines, a ratio of from 1:1.1 to 1:1.35 per exchangeable chlorine atom having proven useful. 1 mole of cyanuric chloride is therefore preferably reacted with from 3.3 to 4.1 moles of alkylenediamine, 1 mole of dichloroaminotriazine is preferably reacted with from 2.2 to 2.7 moles of an alkylenediamine, and 1 mole of diaminochlorotriazine is preferably reacted with from 1.1 to 1.4, in particular from 1.1 to 1.2, moles of alkylenediamine.

In order to trap the hydrochloric acid formed during the reaction, a base, eg. potassium carbonate, sodium carbonate or sodium hydroxide solution, is added. Care should be taken to ensure that the base is not used in excess, since otherwise cleavage of the amide function takes place. For this reason, it is advantageous to add the base gradually so that the pH is kept at about 8.0.

The mixture is refluxed until the reaction is complete, ie. until base is no longer consumed.

Working up and purification of the product are carried out in a conventional manner by a procedure in which the amidoalkylmelamine precipitated from the aqueous solution is filtered off under suction and recrystallized from a suitable solvent, as a rule water, ethanol or an ethanol/water mixture.

For conversion to the aminoalkylmelamine, the amino protective group is eliminated by a conventional method, for example by catalytic hydrogenation in the case of the benzyl carbamates, or by alkaline hydrolysis.

Where hydrolysis is carried out, care should be taken to ensure that the reaction times are kept as short as possible so that the NH function bonded directly to the triazine ring is not attacked.

The novel amidoalkylmelamines and aminoalkylmelamines are useful intermediates for organic syntheses, for example for polyisocyanate polyaddition reactions.

The examples which follow illustrate the invention.

The $^1$H-NMR spectra of the compounds were recorded in DMSO-$d_6$ at 60 MHz, and the chemical shifts δ are based on tetramethylsilane as internal standard. The following abbreviations are used to describe the type of signal: s=singlet, d=doublet, t=triplet, q=quartet, m=multiplet and br=broad signal.

EXAMPLE 1

N,N',N''-Tris-(6-acetamidohexyl)-melamine 18.4 g (0.1 mole) of cyanuric chloride, 56.0 g (0.35 mole) of mono-N-acetylhexamethylenediamine and 41.5 g (0.3 mole) of anhydrous potassium carbonate in 450 ml of dioxane were refluxed for 5 hours, while stirring. The mixture was then filtered while hot, and the filtrate was freed from the solvent. The residue was stirred with 0.5 of water, and the product was filtered off under suction and dried. 40 g (73%) of the tris compound were obtained as colorless crystals. The melting point was 215° C. after recrystallization from ethanol/water.

$^1$H-NMR δ[ppm]=1.3 (s, br., 24H), 1.8 (s, 9H), 3.2 (s, br., 12H), 3.6 (s, br., 3H), 7.8 (s, br., 3H).

| Analysis: | C | H | N |
|---|---|---|---|
| Calculated: | 58.99 | 9.35 | 22.93 |
| Found: | 58.2 | 9.2 | 22.2 |

EXAMPLE 2

N,N'-Bis-(6-acetamidohexyl)-melamine 87.0 g (0.55 mole) of mono-N-acetylhexamethylenediamine were added to a suspension of 41.0 g (0.25 mole) of dichloroaminotriazine in 300 ml of water, and the mixture was heated at the boil. The pH was kept at 8.0 by adding successive amounts of saturated sodium carbonate solution. After 2 hours, the reaction was complete. The mixture was left to cool, and the product was filtered off under suction, washed chloride-free with water and dried to give 95 g (93%) of colorless crystals which, when recrystallized from ethanol/water, had a melting point of 126° C.

$^1$H-NMR δ[ppm]=1.3 (s, br., 16H), 1.8 (s, 6H), 3.2 (m, 8H), 6.0 (s, br., 2H), 6.4 (s, br., 2H), 7.8 (s, br., 2H).

| Analysis:   | C     | H    | N     |
| ----------- | ----- | ---- | ----- |
| Calculated: | 55.86 | 8.88 | 27.43 |
| Found:      | 55.3  | 8.7  | 27.2  |

EXAMPLE 3

N-Mono-(6-acetamidohexyl)-melamine 36.5 g (0.25 mole) of diaminochlorotriazine and 46.8 g (0.30 mole) of mono-N-acetylhexamethylenediamine in 300 ml of water were reacted by a method similar to that described in Example 2 and worked up in a similar manner. Recrystallization from water gave 62 g (93%) of colorless crystals of melting point 94°–96° C.

$^1$H-NMR δ[ppm]=1.3 (s, br., 8H), 1.8 (s, 3H), 3.1 (m, 4H), 6.1 (s, br., 4h), 6.5 (s, br., 1H), 7.8 (s, br., 1H).

| Analysis:   | C     | H    | N     |
| ----------- | ----- | ---- | ----- |
| Calculated: | 49.42 | 7.92 | 36.68 |
| Found:      | 48.2  | 7.7  | 35.1  |

EXAMPLE 4

N,N',N''-Tris-(2-ethoxycarbonylamidoethyl)-melamine 218.0 g (1.65 moles) of mono-N-ethoxycarbonylethylenediamine were added dropwise to a suspension of 92.5 g (0.5 mole) of cyanuric chloride in 500 ml of water. The mixture was then heated slowly, and the pH was kept at 8.1 by successive addition of 25% strength sodium hydroxide solution. Finally, the mixture was refluxed. As soon as sodium hydroxide solution was no longer consumed, the mixture was left to cool and the product was filtered off under suction and recrystallized from ethanol/water to give 197 g (84%) of colorless crystals of melting point 148° C.

$^1$H-NMR δ[ppm]=1.2 (t, 9H), 3.2 (m, 12H), 4.0 (q, 6H), 7.1 (s, br., 3H), 7.7 (s, br., 3H).

| Analysis:   | C     | H    | N     |
| ----------- | ----- | ---- | ----- |
| Calculated: | 45.85 | 7.05 | 26.74 |
| Found:      | 45.5  | 6.9  | 26.6  |

EXAMPLE 5

N,N'-Bis-(2-ethoxycarbonylamidoethyl)-melamine 33 g (0.2 mole) of dichloroaminotriazine and 58 g (0.44 mole) of mono-N-ethoxycarbonylethylenediamine in 160 ml of water were reacted and the mixture was worked up, these operations being carried out similarly to Example 4. Recrystallization from methanol/water gave 58 g (81%) of colorless crystals of melting point 146° C.

$^1$H-NMR δ[ppm]=1.2 (t, 6H), 3.2 (m, 8H), 4.0 (q, 4H), 6.1 (s, br., 2H), 6.4 (s, br., 2H), 7.0 (s, br., 2H).

| Analysis:   | C     | H    | N     |
| ----------- | ----- | ---- | ----- |
| Calculated: | 43.81 | 6.79 | 31.44 |
| Found:      | 43.6  | 6.7  | 31.4  |

EXAMPLE 6

N-Mono-(2-ethoxycarbonylamidoethyl)-melamine 43.8 g (0.3 mole) of diaminochlorotriazine and 47.4 g (0.36 mole) of mono-N-ethoxycarbonylethylenediamine in 270 ml of water were reacted and the mixture was worked up, these operations being carried out similarly to Example 4. Recrystallization from water gave 58.2 g (80%) of colorless crystals of melting point 198° C.

$^1$H-NMR δ[ppm]=1.2 (t, 3H), 3.2 (m, 4H), 4.0 (q, 2H), 6.1 (s, br., 4H), 6.4 (s, br., 1H), 7.1 (s, br., 1H).

| Analysis:   | C     | H    | N     |
| ----------- | ----- | ---- | ----- |
| Calculated: | 39.83 | 6.27 | 40.64 |
| Found:      | 39.3  | 6.1  | 39.8  |

EXAMPLE 7

N,N',N''-Tris-(6-benzyloxycarbonylamidohexyl)-melamine 1.85 g (0.01 mole) of cyanuric chloride and 10.0 g (0.04 mole) of mono-N-carbobenzyloxyhexamethylenediamine in 100 ml of water were reacted and the mixture was worked up, these operations being carried out similarly to Example 4. Recrystallization from ethanol gave 5.2 g (63%) of colorless crystals of melting point 98° C.

$^1$H-NMR δ[ppm]=1.3 (s, br., 24H), 3.1 (m, 12H), 5.0 (s, 6H), 6.4 (s, br., 3H), 7.2 and 7.3 (m and s, 18H).

| Analysis:   | C     | H    | N     |
| ----------- | ----- | ---- | ----- |
| Calculated: | 65.43 | 7.69 | 15.26 |
| Found:      | 64.9  | 7.2  | 15.3  |

EXAMPLE 8

N,N'-Bis-(6-benzyloxycarbonylamidohexyl)-melamine 5.8 g (0.035 mole) of dichloroaminotriazine and 23.0 g (0.092 mole) of mono-N-carbobenzyloxyhexamethylenediamine in 170 ml of water were reacted and the mixture was worked up, these operations being carried out similarly to Example 4. Recrystallization from a 2:1 ethanol/water mixture give 18.9 g (91%) of colorless crystals of melting point 101° C.

$^1$H-NMR δ[ppm]=1.3 (s, br., 16H), 3.1 (m, 8H), 5.0 (s, 4H), 5.9 (s, br., 2H), 6.3 (s, br., 2H), 7.2 and 7.3 (m and s, 12H).

| Analysis:   | C     | H    | N     |
| ----------- | ----- | ---- | ----- |
| Calculated: | 62.82 | 7.48 | 18.91 |
| Found:      | 62.8  | 7.1  | 18.6  |

EXAMPLE 9

N-Mono-(6-benzyloxycarbonylamidohexyl)-melamine 7.3 g (0.050 mole) of diaminochlorotriazine and 14.0 g (0.056 mole) of mono-N-carbobenzyloxyhexamethylenediamine in 100 ml of water were reacted as described in Example 4. After the mixture had been cooled, a virtually colorless oil separated out. The oil phase was separated off, and the aqueous phase was extracted with ethyl acetate. The combined organic phases were then washed with water and dried over sodium sulfate, and the solvent was removed under reduced pressure. 17.3 g (96%) of a colorless oil were obtained, and this oil was identified unambiguously as N-mono-(6-benzyloxycarbonylamidohexyl)-melamine by spectroscopy ($^1$H-NMR, 13C-NMR, IR, MS). $^1$H-NMR δ[ppm]=1.3 (s, br., 8H), 3.1 (m, 4H), 5.0 (s, 2H), 6.3 (m, 5H), 7.2 and 7.3 (m and s, 6H).

| Analysis: | C | H | N |
|---|---|---|---|
| Calculated: | 56.81 | 7.01 | 27.28 |
| Found: | 57.4 | 7.1 | 24.6 |

EXAMPLE 10

N,N',N''-Tris-(2-aminoethyl)-melamine 25.5 g (0.05 mole) of N,N',N''-tris-(2-ethoxycarbonylamidoethyl)-melamine (from Example 4) were boiled for 8 hours in a solution of 36 g (0.90 mole) of NaOH in 300 ml of water. A clear solution was formed. The sodium hydroxide solution was neutralized with 43.0 g (0.45 mole) of concentrated sulfuric acid, and the solvent was stripped off. The solid colorless residue was extracted continuously with ethanol. Removal of the ethanol under reduced pressure gave 10 g (78%) of a pale yellow oil, which was identified unambiguously as N,N',N''-tris-(2-aminoethyl)-melamine by $^1$H-NMR, $^{13}$C-NMR and IR spectroscopy.

$^1$H-NMR δ[ppm]=1.9 (s, br., 6H), 2.6 (t, 6H), 3.1 (t, 6H), 6.6 (s, br., 3H).

| Analysis: | C | H | N |
|---|---|---|---|
| Calculated: | 42.34 | 8.29 | 49.37 |
| Found: | 42.5 | 8.5 | 47.9 |

EXAMPLE 11

N,N'-Bis-(2-aminoethyl)-melamine 54.0 g (0.15 mole) of N,N'-bis-(2-ethoxycarbonylamidoethyl)-melamine (from Example 5) were hydrolyzed for 6 hours in a solution of 51.0 g (1.30 moles) of sodium hydroxide in 300 ml of water as described in Example 10, and the mixture was then neutralized with 61.0 g (0.65 mole) of concentrated sulfuric acid. Working up in a manner similar to that described in Example 10, and recrystallization from ethanol/ether gave 25.0 g (79%) of colorless crystals of melting point 135° C.

$^1$H-NMR δ[ppm]=1.8 (s, br., 4H), 2.6 (t, 4H), 3.2 (t, 4H), 6.2 (s, br., 2h), 6.7 (s, br., 2H).

| Analysis: | C | H | N |
|---|---|---|---|
| Calculated: | 39.61 | 7.60 | 52.79 |
| Found: | 39.8 | 7.5 | 52.3 |

EXAMPLE 12

N-Mono-(2-aminoethyl)-melamine 60 g (0.25 mole) of N-mono-(2-ethoxycarbonylamidoethyl)-melamine (from Example 6) were hydrolyzed for 3 hours in a solution of 40 g (1.0 mole) of sodium hydroxide in 300 ml of water as described in Example 10, and the mixture was then evaporated down to about 70 ml. When the mixture had cooled, the precipitate which had separated out was filtered off under suction, boiled several times with ethanol and filtered off. The ethanol filtrates were evaporated to dryness, and the resulting residue was recrystallized from water. 28 g (66%) of colorless crystals of melting point 112° C. were obtained.

$^1$H-NMR δ[ppm]=2.3 (s, br., 2H), 2.6 (t, 2H), 3.2 (t, 2H), 6.4 (s, br., 4H), 6.8 (s, br., 1H).

| Analysis: | C | H | N |
|---|---|---|---|
| Calculated: | 35.50 | 6.55 | 57.95 |
| Found: | 36.0 | 6.5 | 57.9 |

EXAMPLE 13

N-Mono-(6-aminohexyl)-melamine 7.2 g (0.02 mole) of N-mono-(6-benzyloxycarbonylamidohexyl)-melamine (from Example 9) were hydrogenated for 20 hours under a hydrogen pressure of 30 bar and at room temperature, in a mixture of 100 ml of water and 100 ml of glacial acetic acid, using 0.2 g of 10% strength palladium on active carbon as a catalyst. The catalyst was then filtered off, and the mixture was evaporated to dryness under reduced pressure. The residue was dissolved in 50 ml of hot water, and the solution was filtered again and rendered alkaline with 50% strength sodium hydroxide solution, the product being precipitated. 2.5 g (56%) of colorless crystals of melting point 225°–228° C. were obtained. The product was recrystallized from a 2:1 water/ethanol mixture.

$^1$H-NMR δ[ppm]=1.3 (s, br., 8H), 2.1 (s, 2H), 2.5 (m, 2H), 3.2 (m, 2H), 6.0 (s, br., 4H), 6.4 (t, 2H).

| Analysis: | C | H | N |
|---|---|---|---|
| Calculated: | 47.98 | 8.50 | 43.52 |
| Found: | 47.7 | 8.7 | 42.1 |

EXAMPLE 14

N,N'-Bis-(6-aminohexyl)-melamine 17.8 g (0.03 mole) of N,N'-bis-(6-benzyloxycarbonylamidohexyl)-melamine (from Example 8) were hydrogenated for 20 hours under a hydrogen pressure of 30 bar and at room temperature, in 100 ml of ethanol and 100 ml of glacial acetic acid, using 0.6 g of 10% strength palladium on active carbon as a catalyst. The catalyst was then filtered off, and the mixture was evaporated to dryness under reduced pressure. The residue was freed from any adhering glacial acetic acid by chromatography over a strongly basic ion exchanger. Removal of the ethanol and drying under reduced pressure gave 7.0 g (72%) of a virtually colorless oil.

$^1$H-NMR δ[ppm]=1.3 (s, br., 16H), 2.2 (s, 4H), 2.5 (m, 4H), 3.2 (m, 4H), 6.0 (s, br., 2H), 6.4 (s, br., 2H).

| Analysis: | C | H | N |
|---|---|---|---|
| Calculated: | 55.52 | 9.94 | 34.53 |
| Found: | 55.0 | 10.0 | 34.1 |

EXAMPLE 15

N,N',N''-Tris-(6-aminohexyl)-melamine 21.2 g (0.03 mole) of N,N',N''-tris-(6-benzyloxycarbonylamidohexyl)-melamine (from Example 7) were hydrogenated as described in Example 14. Working up by a similar procedure gave 11.3 g (89%) of a virtually colorless oil.

$^1$H-NMR $\delta$[ppm]=1.3 (s, br., 24H), 2.0 (s, 6H), 2.5 (m, 6H), 3.2 (m, 6H), 6.3 (s, br., 3H).

| Analysis: | C | H | N |
|---|---|---|---|
| Calculated: | 59.54 | 10.71 | 29.76 |
| Found: | 59.1 | 10.8 | 29.2 |

We claim:

1. An N,N',N''-tris-aminoalkylmelamine of the formula

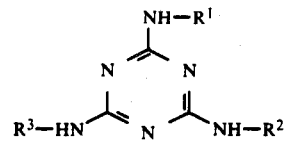

where $R^1$, $R^2$ and $R^3$ are each a radical $-(CH_2)_n-NH_2$ and n is from 2 to 10.

2. The compound of the formula of claim 1 wherein n is from 2 to 6.

3. The compound of the formula of claim 1 wherein n is 6.

4. The compound of the formula of claim 1 wherein n is 2.

* * * * *